(12) United States Patent
Isaza

(10) Patent No.: US 11,413,415 B2
(45) Date of Patent: Aug. 16, 2022

(54) ESTIMATING LUNG COMPLIANCE AND LUNG RESISTANCE USING A PRESSURE CONTROLLED BREATH TO ALLOW ALL RESPIRATORY MUSCLE RECOIL GENERATED PRESSURE TO VANISH

(71) Applicant: KONINKLIJKE PHILIPS N.V., Eindhoven (NL)

(72) Inventor: Fernando Jose Isaza, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 698 days.

(21) Appl. No.: 16/339,768

(22) PCT Filed: Sep. 25, 2017

(86) PCT No.: PCT/EP2017/074154
§ 371 (c)(1),
(2) Date: Apr. 5, 2019

(87) PCT Pub. No.: WO2018/065246
PCT Pub. Date: Apr. 12, 2018

(65) Prior Publication Data
US 2020/0038611 A1 Feb. 6, 2020

Related U.S. Application Data

(60) Provisional application No. 62/405,405, filed on Oct. 7, 2016.

(51) Int. Cl.
*A61M 16/00* (2006.01)
*A61M 16/20* (2006.01)

(52) U.S. Cl.
CPC ........ *A61M 16/026* (2017.08); *A61M 16/205* (2014.02); *A61M 2016/0027* (2013.01);
(Continued)

(58) Field of Classification Search
CPC .................................................. A61M 2230/46
See application file for complete search history.

(56) References Cited

U.S. PATENT DOCUMENTS 7,918,223 B2 4/2011 Soliman et al.
8,424,521 B2 4/2013 Jafari et al.
(Continued)

FOREIGN PATENT DOCUMENTS

WO 9722377 A1 6/1997
WO 2007134099 A2 11/2007
(Continued)

OTHER PUBLICATIONS

Lucangelo et al: "Respiratory Mechanics Derived From Signals in the Ventilator Circuit" Respiratory, Daedalus Enterprises, Inc., vol. 50, No. 1, Jan. 2005, pp. 55-67.
(Continued)

*Primary Examiner* — Margaret M Luarca
*Assistant Examiner* — Cana A Gallegos
(74) *Attorney, Agent, or Firm* — Daniel H. Brean

(57) ABSTRACT

A mechanical ventilator (10) is controlled by an electronic processor (14) to provide respiratory support to a patient (12) using a pressure controlled ventilation mode while being monitored by an airway pressure sensor (30) and an airway flow sensor (32). The electronic processor also controls the ventilator to perform a respiratory system measurement process (44) including: controlling the ventilator to provide a pressure controlled breath at a preset pressure ($P_{preset}$) over an extended inspiratory breath interval that is extended by an extension time interval ($T_{IE}$) beyond end of physiological inspiration; controlling an exhalation valve (40) at least during the extension time interval to maintain airway pressure at the preset pressure ($P_{preset}$). Lung compliance or elastance is determined from
(Continued)

airway pressure measurements and airway flow measurements acquired during the extended inspiratory breath interval.

14 Claims, 3 Drawing Sheets

(52) U.S. Cl.
    CPC . *A61M 2016/0036* (2013.01); *A61M 2205/50* (2013.01); *A61M 2230/46* (2013.01)

(56) References Cited

U.S. PATENT DOCUMENTS

| | | | |
|---|---|---|---|
| 2005/0284476 A1 | 12/2005 | Blanch et al. | |
| 2007/0272241 A1* | 11/2007 | Sanborn | A61M 16/0051 128/204.23 |
| 2012/0226444 A1* | 9/2012 | Milne | A61M 16/0051 702/19 |
| 2012/0247471 A1* | 10/2012 | Masic | A61M 16/026 128/204.23 |
| 2013/0174846 A1* | 7/2013 | Stenqvist | A61M 16/204 128/204.23 |
| 2014/0048072 A1* | 2/2014 | Angelico | A61M 16/0063 128/204.23 |
| 2014/0194767 A1* | 7/2014 | Zheng | G09B 23/288 600/538 |
| 2016/0206837 A1* | 7/2016 | Dong | A61M 16/20 |

FOREIGN PATENT DOCUMENTS

| | | |
|---|---|---|
| WO | 2010099373 A1 | 9/2010 |
| WO | 2013098717 A1 | 7/2013 |
| WO | 2016098020 A1 | 6/2016 |

OTHER PUBLICATIONS

Mcario et al.: "Noninvasive Estimation of Respiratory Mechanics in Spontaeously Breathing Ventilated Patients: a Contrained Optimization Approach"; IEEE Transactions On Biomedical Engineering, vol. 63, No. 4, Apr. 1, 2016, pp. 775-787.

\* cited by examiner

ESTIMATING LUNG COMPLIANCE AND LUNG RESISTANCE USING A PRESSURE CONTROLLED BREATH TO ALLOW ALL RESPIRATORY MUSCLE RECOIL GENERATED PRESSURE TO VANISH

CROSS-REFERENCE TO PRIOR APPLICATIONS

This application is the U.S. National Phase application under 35 U.S.C. § 371 of International Application No. PCT/EP2017/074154, filed on Sep. 25, 2017, which claims the benefit of U.S. Provisional Patent Application No. 62/405,405, filed on Oct. 7, 2016. These applications are hereby incorporated by reference herein.

FIELD

The following relates generally to the respiratory arts, mechanical ventilation arts, respiratory monitoring arts, and related arts.

BACKGROUND

Measurement of respiratory parameters of a mechanically ventilated patient, including the lung compliance $C_L$ (or, equivalently, lung elastance $E_L=1/C_L$) and lung resistance $R_L$, is useful for numerous purposes. The values per se can be used as clinical diagnostic data. For example, a decrease in the lung compliance can be an indicator of onset of Acute Respiratory Distress Syndrome (ARDS). As another example, an increase in lung resistance can indicate possible secretion accumulation. The values of $C_L$ and $R_L$ are also parameters of the Equation of Motion of the Lungs which relates the airway pressure $P_y(t)$, lung air flow $Q(t)$, lung volume $V_L(t)$ (a time integral of Q), and respiratory muscle pressure $P_{mus}(t)$ applied by the diaphragm and chest muscles of the patient. Thus, if the airway pressure and airway flow are measured (which is usually done as standard monitoring of a mechanically ventilated patient) then knowledge of $R_L$ and $C_L$ permits determination of the respiratory muscle pressure and hence the work of breathing (WoB) or power of breathing (PoB). This, in turn, can be used for various purposes such diagnosing health of the respiratory system, or calibrating respiratory support provided by the mechanical ventilator to limit muscle fatigue while maintaining therapeutically effective respiration. Various approaches are known for estimating the respiratory parameters. In the so-called pause maneuver, the expiration valve is closed for a time interval so that no air can leave the lungs. This allows the lung pressure to equilibrate, permitting assessment of the respiratory parameters while minimizing overpressure of the lungs. Other approaches are known which do not utilize the pause maneuver.

The following discloses new and improved systems and methods.

SUMMARY

In one disclosed aspect, a respiratory device is disclosed, including an airway pressure sensor, an airway flow sensor, and an electronic processor programmed to control a mechanical ventilator to provide respiratory support using a pressure controlled ventilation mode and to perform a respiratory system measurement process. The process includes: controlling the mechanical ventilator to provide a pressure controlled breath at a preset pressure over an extended inspiratory breath interval that is extended by an extension time interval beyond an end of inspiration indicated by a zero crossing of the airway flow; controlling an exhalation valve at least during the extension time interval to maintain airway pressure estimated by the airway pressure sensor at or near the preset pressure; during the extended inspiratory breath interval, acquiring airway pressure estimates from the airway pressure sensor and airway flow estimates from the airway flow sensor; and determining lung compliance or elastance from the airway pressure estimates and the airway flow estimates acquired during the extended inspiratory breath interval.

In another disclosed aspect, a ventilator device includes a mechanical ventilator, an airway pressure sensor, an airway flow sensor, and an electronic processor. The processor is programmed to control the mechanical ventilator to provide respiratory support including applying a preset pressure during inhalation, and to perform a respiratory system measurement process including: controlling the mechanical ventilator to provide a pressure controlled breath at the preset pressure over an extended inspiratory breath interval that is extended by an extension time interval beyond end of inspiration; controlling an exhalation valve during the extended inspiratory breath interval to maintain airway pressure estimated by the airway pressure sensor at the preset pressure; using the airway pressure sensor, measuring an end of inhalation (eoi) airway pressure at a time when the airway flow estimate is zero; using the airway pressure sensor, measuring a beginning of inhalation (boi) airway pressure at the beginning of the inhalation time period; and determining lung compliance or elastance based on (i) a change in lung volume produced by the pressure controlled breath and computed as a time integral of airway flow estimates by the airway flow sensor and (ii) a difference between the eoi airway pressure and the boi airway pressure.

In another disclosed aspect, a ventilator method is disclosed. Respiratory support is provided using a mechanical ventilator including applying a preset pressure during inhalation. The mechanical ventilator is controlled to provide a pressure controlled breath at the preset pressure over an extended inspiratory breath interval that is extended by an extension time interval beyond end of inspiration. An exhalation valve is controlled during the extended inspiratory breath interval to maintain airway pressure estimated by the airway pressure sensor at the preset pressure. Using an airway pressure sensor, a beginning of inhalation (boi) airway pressure is measured at the beginning of the inhalation time period and an end of inhalation (eoi) airway pressure is measured at a time when airway flow estimated by an airway flow sensor is zero. A change in lung volume produced by the pressure controlled breath is computed as a time integral of airway flow estimates acquired using the airway flow sensor. Lung compliance or elastance is determined based on (i) the change in lung volume produced by the pressure controlled breath and (ii) a difference between the eoi airway pressure and the boi airway pressure. The computing and the determining are suitably performed by an electronic processor.

One advantage resides in providing for estimating respiratory parameters under conditions mimicking therapeutic pressure-controlled mechanical ventilation such as pressure support ventilation (PSV) or pressure-controlled ventilation (PCV).

Another advantage resides in providing such estimation accurately for an active patient who is exerting respiratory effort.

Another advantage resides in providing such estimation while suppressing or minimizing any lung pressure overshoot.

Another advantage resides in providing such estimation including accounting for dependence of lung resistance on airway flow.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Conventional approaches that employ the pause maneuver in measuring respiratory parameters have the disadvantage of potentially measuring the parameters at an artificially high lung pressure as the lung pressure can "overshoot" during the time interval over which the exhalation valve is closed. (By "artificially high" it is meant that the lung pressure is higher than that employed in the therapeutic mechanical ventilation). Since $C_L$ and $R_L$ can depend on lung pressure, the resulting measured $R_L$ and $C_L$ (or $E_L$) may not accurately represent lung characteristics during therapeutic mechanical ventilation. Other approaches for measuring the respiratory parameters do not utilize the pause maneuver, and hence do not introduce lung pressure overshoot. However, these approaches still usually assume a passive patient ($P_{mus}=0$).

Pressure-controlled ventilation modes such as pressure controlled ventilation (PCV) or pressure support ventilation (PSV) are commonly used to provide respiratory assistance for actively breathing patients. For example, in PSV the inhalation effort by the patient is typically detected as an onset of air flow into the lungs and in response the PSV provides positive pressure to assist the inhalation effort. As an example, respiratory parameters measured during a pause maneuver are acquired during physiological conditions that are at substantial variance to the conditions present during PSV, so that the resulting $C_L$ and $R_L$ values may be inaccurate for the current PSV settings used to ventilate the patient.

Figure 1:
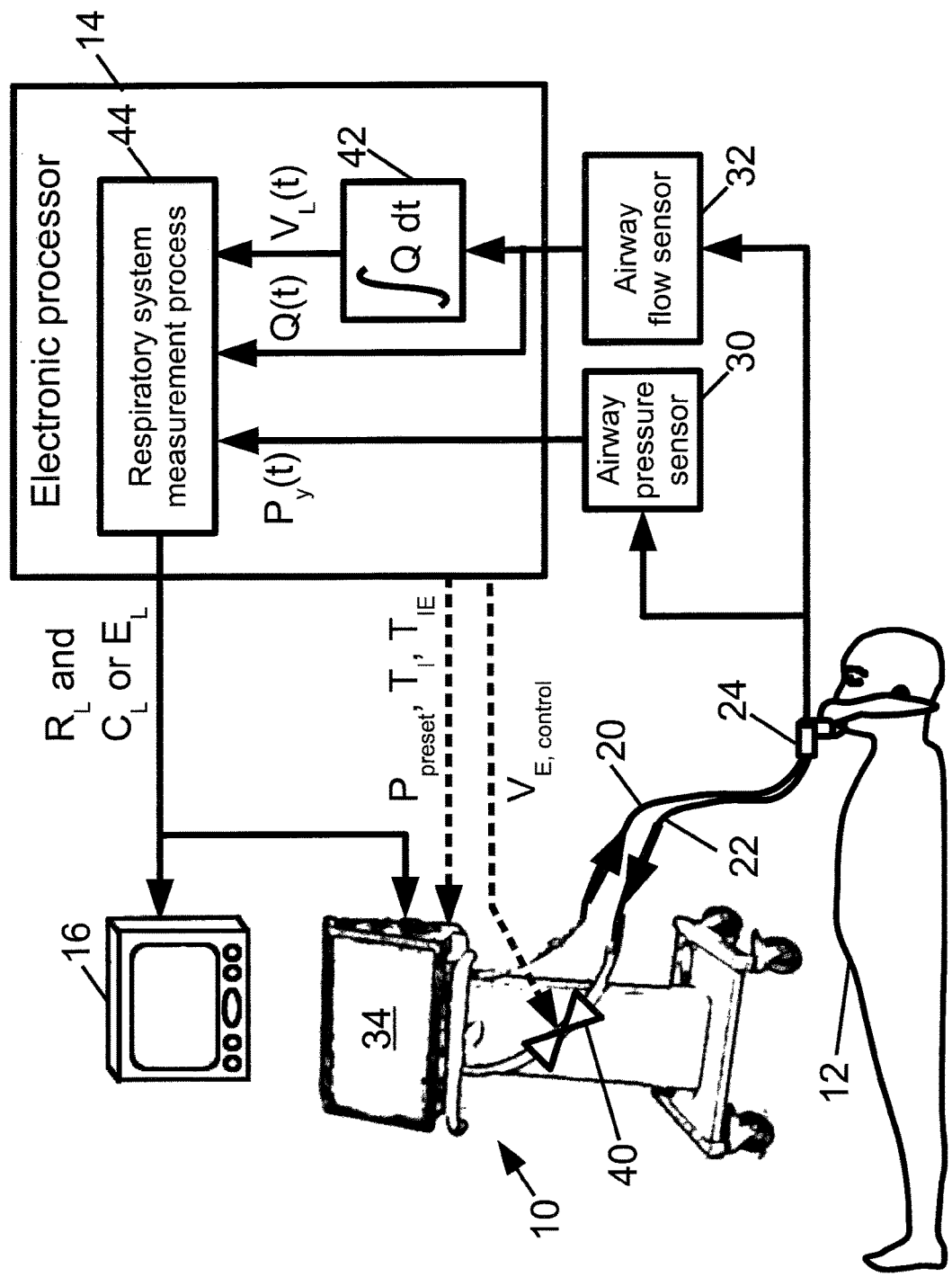
FIG. 1 diagrammatically illustrates a mechanical ventilation device including a mechanical ventilator and an electronic processor (which may be integral with the mechanical ventilator or with some other electronic component) that controls the mechanical ventilator to perform a respiratory system measurement process as disclosed herein.

With reference to FIG. 1, some improvements are described in the context of a mechanical ventilation device including a mechanical ventilator 10 that delivers therapeutic ventilation to a patient 12, and an electronic processor 14 (which may be integral with the mechanical ventilator 10 or with some other electronic component, such as an illustrative patient monitor device 16) that controls the mechanical ventilator 10 to perform a respiratory system measurement process as disclosed herein. More particularly, the ventilator 10 is connected with the patient 12 via an inlet air hose 20 and an exhaust air hose 22. The interface with the patient's respiratory system is via a non-invasive face mask 24, as illustrated, or alternatively may be via an invasive tracheal tube (not shown). Suitable sensors including an illustrative airway pressure sensor 30 and an illustrative airway flow sensor 32 are provided to monitor the patient's respiration. While the sensors 30, 32 are diagrammatically illustrated in FIG. 1, it will be appreciated that these sensors 30, 32 may be variously embodied, e.g. as components integral with the face mask 24, or located inside the housing of the mechanical ventilator 10, or mounted externally on the air hoses 20, 22, or so forth. The sensors 30, 32 may have any practical configuration, e.g. in-line sensors, side-stream sensors, or so forth. In addition to the illustrative sensors 30, 32, other respiratory sensors may be provided such as a capnography, and the patient 12 may be monitored by other physiological sensors (not shown), e.g. to monitor heart rate, blood pressure, $SpO_2$, or so forth. The illustrative mechanical ventilator 10 includes a display 34 typically providing display of the various measurements such as airway pressure $P_y(t)$ measured using the airway pressure sensor 30, airway flow $Q(t)$ measured using the airway flow sensor 32, and optionally other measured parameters (pulse, $SpO_2$, $CO_2$ measured by a capnography, et cetera). In the illustrative examples, the airway pressure sensor 30 is located at the patient port (e.g. tracheal tube or respiratory mask) so as to directly measure the airway pressure $P_y(t)$, and likewise the airway flow sensor 32 is located at the patient port to directly measure the airway air flow $Q(t)$. More generally, the airway pressure sensor 30 may be any sensor that is used to estimate the airway pressure $P_y(t)$, e.g. the airway pressure sensor 30 may as a further illustration be a pressure sensor located elsewhere in the respiratory circuit (i.e. not at the patient port) that measures a pressure from which the airway pressure $P_y(t)$ can be reliably estimated, e.g. based on a known flow resistance between the patient port and the measurement point. Likewise, the airway flow sensor 32 may be any sensor that is used to estimate the airway flow $Q(t)$, e.g. the airway flow sensor 32 may as a further illustration be a flow sensor located elsewhere in the respiratory circuit that measures a flow from which the airway air flow $Q(t)$ can be reliably estimated. In the following, the term "measured" with be used in conjunction with $P_y(t)$ and $Q(t)$ but it is to be understood that more generally these values may be estimated from measurements of other associated quantities. These may be displayed as numbers, trend lines, and/or so forth. The display 34 may also serve as a user interface, e.g. including touch-screen input capability or having auxiliary user input devices (not shown) such as a physical keyboard, trackball, or so forth. As a user interface, the display 34 may display information such as the fraction of inspired oxygen ($FiO_2$) controlled by the setting of an oxygen canister, the preset pressure $P_{preset}$ of pressure-controlled breaths delivered to the patient 12 by the ventilator 10 in accord with a chosen ventilator mode such as Pressure Support Ventilation (PSV) mode, Pressure Control Ventilation (PCV), or another pressure-based ventilation mode. Other salient information for monitoring the mechanical ventilation and the status of the patient 12 may also/alternatively be displayed on the display 34 of the mechanical ventilator 10.

As is typical for mechanical ventilator devices, an exhaust valve 40 is also provided. The illustrative exhaust valve 40 is mounted in-line on the exhaust air hose 22, but other configurations are contemplated, e.g. the exhaust valve may be mounted as a component inside the housing of the mechanical ventilator 10 or may be integral with the face mask 24. Typically, during inhalation the exhaust valve 40 is closed to prevent exhalation (that is, to block air flow out of the lungs through the exhaust air line 22), and the exhaust valve 40 is opened during the exhalation phase to permit expiration (i.e. air flow out of the lungs through the exhaust air line 22).

The illustrative patient monitor 16 is optional; if provided it may provide some of the display functionality just described (e.g. displaying heart rate, respiration rate, $SpO_2$, or so forth), enabling user input for various control operations, and/or so forth.

In some suitable embodiments, the electronic processor 14 is a microprocessor or microcontroller operatively connected with auxiliary components such as a read-only memory (ROM), electronically erasable programmable read-only memory (EEPROM), flash memory, or so forth storing instructions readable and executable by the microprocessor or microcontroller to perform functions described herein, a random access memory (RAM) to provide temporary data storage, interfacing components for generating and outputting control signals for controlling the mechanical ventilator 10, sensor couplings or input interfaces for reading measurements output by the sensors 30, 32, and so forth. As previously mentioned, the electronic processor 14 may be integral with and disposed inside the housing of the mechanical ventilator 10 (e.g. the electronic processor 14 may be the electronics or electronic controller of the ventilator 10), or may be the processor of a separate component such as a computer (not shown) or the patient monitor 16. The electronic processor 14 is programmed to perform various functions. If it is the controller of the mechanical ventilator 10 then the electronic processor 14 is programmed to operate the mechanical ventilator 10 to perform therapeutic ventilation in accord with a pressure-controlled ventilation mode (e.g. PSV or PCV), as well as to receive sensor data from the sensors 30, 32 and to display the sensor data and salient ventilator data on the display 34.

Of particular interest, the electronic processor 14 is programmed to receive or estimate airway flow measurements Q(t) from the airway flow sensor 32 and to perform an integration process 42 to time-integrate the airway flow measurements to compute the lung volume $V_L(t) = \int Q(t) dt$ where t denotes time and the integral is over some defined time period, e.g. starting at the start of inhalation and terminating at the end of inhalation to determine air volume inhaled over a single inhalation period. It will be appreciated that in some embodiments this integration is performed via some other processor and the result $V_L(t)$ then input to the electronic processor 14—for example, the airway flow sensor 32 may include such an electronic processor programmed to perform the integration process 42 so that the airway flow sensor is a combined air flow/air volume sensor.

The electronic processor 14 is further programmed to perform a respiratory system measurement process 44 as disclosed herein. The respiratory system measurement process 44 is typically performed during ventilation in Pressure Support Ventilation (PSV) mode or Pressure Control Ventilation (PCV) mode performed by the ventilator 10 (either under control of the processor 14 or under control of another processer not shown). In the process 44, a pressure-controlled (PC) breath is applied at a preset pressure (preferably equal to the preset pressure $P_{preset}$ of the PSV or PCV), with enough inspiratory (or inhalation) time ($T_I$) to allow for a complete inhalation to occur. The PC breath is then continued for an additional extension time interval ($T_{IE}$) during which all the respiratory muscle activity is allowed to cease while the pressure in the lungs equilibrate at or near the preset pressure $P_{preset}$ in the mechanical ventilator tubing circuit (e.g. air hoses 20, 22).

The inhalation time period $T_I$ may in some embodiments be set as a detected inhalation time period of a breath averaged over a defined number of breaths, e.g. over 10 breaths in some embodiments. The inhalation time period may be detected using any of various techniques, e.g. by detecting a ramp-up of the air flow measured by the airway flow sensor 32 indicating the start of an inhalation and subsequent cessation of the measured air flow indicating the end of the inhalation. (In general, the physiological breath phases may be suitably determined by the direction of the flow of gas in or out of the airways/lungs).

In some illustrative embodiments, the inhalation time $T_I$ is set equal to the 10 breath average of the previous inhalation periods for the last 10 valid PC breaths of the PSV or PCV controlled mechanical ventilation. A "valid" PSV or PCV breath is a breath that does not terminate via truncation of the breath due to a High Inspiratory Pressure alarm (HIP), a tubing circuit occlusion or a tubing circuit disconnect. As an example, if the mechanical ventilator 10 employs an $E_{sens}$ setting to adjust the termination criteria for PSV breaths, then this may be used to evaluate $T_I$—for this purpose, it is preferable for $E_{sens}$ to be set temporarily, for the duration of the inhalation time ($T_I$) estimation, to a low value such as 1% (or preferably as low as the $E_{sens}$ setting range of the particular mechanical ventilator allows).

The additional extension time interval $T_{IE}$ should be long enough to ensure the patient's respiratory muscle activity has ceased, but not so long as to create undue respiratory distress. In some embodiments, the extension time interval $T_{IE}$ is between 0.3 seconds and 0.7 seconds inclusive, although a longer or shorter pause time period is contemplated. In specific illustrative embodiments described herein, $T_{IE}$=0.5 sec is used. In some embodiments, the extension time interval $T_{IE}$ is chosen as a patient-specific extension time interval determined based on airflow measurements made after end-of-inspiration (eoi) over several breaths. In general, the goal is to set $T_{IE}$ long enough for all respiratory muscle recoil-generated pressure to vanish. It would be straightforward to set $T_{IE}$ if the respiratory muscle pressure as a function of time, $P_{mus}(t)$, were known in real-time. In practice, however, this is not a measured quantity, and is not readily estimated in real-time. As a surrogate, it is known that the air flow reverses at the end of physiological inspiration due to respiratory muscle recoil. Thus, the air flow crosses zero as the respiratory muscle pressure relaxes at end-of-inspiration. When this reversed air flow returns to zero, it is known that all respiratory muscle recoil-generated pressure has vanished. Accordingly, in some embodiments, $T_{IE}$ is set to the time interval between the first zero crossing of the air flow (which marks the end of physiological inspiration, i.e. the end of the inhalation time $T_I$) and the next zero crossing of the air flow (which marks a definitive end of respiratory muscle recoil-generated pressure). For greater accuracy, $T_{IE}$ is preferably estimated over a defined number of breaths, e.g. the same number of breaths (e.g. 10 in an illustrative example) used to estimate $T_I$.

Thus, the process 44 includes the electronic processor 14 controlling the mechanical ventilator 10 to provide a pressure controlled (PC) breath at the chosen preset pressure $P_{preset}$ over an extended inspiratory breath interval ($T_I+T_{IE}$) consisting of an inhalation time period $T_I$ followed by an extension time interval $T_{IE}$. Preferably, the chosen preset pressure $P_{preset}$ is similar to or the same as the preset pressure applied by the PSV or PCV ventilation so that the resulting $R_L$ and $C_L$ or $E_L$ parameters are appropriate for the PSV or PCV ventilation (this recognizes that $R_L$ and $C_L$ or $E_L$ can have dependence on the lung pressure).

The PC breath over the extended inspiratory breath interval ($T_I+T_{IE}$) has some similarities with a conventional pause maneuver. However, there is a significant distinction: in the PC breath of the process 44, the exhalation valve 40 is controlled at least during the extension time interval $T_{IE}$ (and more typically over the entire extended inspiratory breath interval $T_I+T_{IE}$) to maintain airway pressure $P_y$ measured by the airway pressure sensor 30 at the preset pressure $P_{preset}$. In diagrammatic FIG. 1, this is indicated by a control signal $V_{E,control}$ sent by the electronic processor 14 to the exhalation valve 40 providing this control based on the feedback of the measured $P_y(t)$ values provided by the airway pressure sensor 30. In the case of a passive patient who is not exerting any respiratory muscle pressure ($P_{mus}(t)=0$, see FIG. 2), it is generally possible to keep the measured airway pressure $P_y$ close to $P_{preset}$ since there is no perturbing respiratory effort. In the case of an active patient who is making respiratory effort, $P_{mus}(t)$ is not zero (see FIG. 3)—this perturbing nonzero $P_{mus}(t)$ is compensated by adjustment of the exhalation valve 40 to keep $P_{preset}$. In this way, it is $P_y(t) \cong P_{preset}$. In this way, it is generally possible to keep the measured airway pressure $P_y$ close to $P_{preset}$ over the extended inspiratory breath interval ($T_I+T_{IE}$), with some slight deviations due to imperfect control. It is also noted that $P_y(t)$ exhibits an initial ramp-up period as the pressure builds up, so that $P_y$ will be below $P_{preset}$ until the ramp-up is complete (see FIGS. 2 and 3).

At the end of the pressure-controlled breath of duration $T_I+T_{IE}$, lung compliance $C_L$ or elastance $E_L=1/C_L$ is determined from the airway pressure measurements $P_y(t)$ and the airway flow measurements $Q(t)$ acquired during the extended inspiratory breath interval $T_I+T_{IE}$. In some embodiments, this is done as follows. An end of inhalation (eoi) airway pressure $P_{eoi}$ is determined as an airway pressure measurement acquired during the extension time interval $T_{IE}$ at an eoi measurement time when the airway flow measurement is zero (i.e. when $Q(t)=0$). A beginning of inhalation (boi) airway pressure $P_{boi}$ is similarly determined as an airway pressure measurement acquired at a boi measurement time at the beginning of the inhalation time period, e.g. when the airway flow crosses from negative to positive (i.e. at $Q(t)=0$) indicating the onset of the inhalation. The lung compliance or elastance is then determined as a ratio of: (i) a change in lung volume ($\Delta V_L$) produced by the pressure controlled breath and computed as a time integral of the airway flow measurements $Q(t)$ (that is, computed using the integration process 42 performed over the inhalation period); and the difference ($P_{eoi}-P_{boi}$) between the eoi airway pressure $P_{eoi}$ and the boi airway pressure $P_{boi}$. In some embodiments, the change in lung volume $\Delta V_L$ produced by the pressure controlled breath is computed as a time integral of the airway flow measurements between the boi measurement time and the eoi measurement time. Expressed as a formula, the lung compliance ($C_L$) may be calculated as follows:

$$C_L = \frac{\Delta V_L}{P_{eoi} - P_{boi}} \quad (1)$$

or, equivalently, the lung elastance $E_L=1/C_L$ may be calculated as follows:

$$E_L = \frac{P_{eoi} - P_{boi}}{\Delta V_L} \quad (2)$$

In one particular embodiment, the following values are used. The end point for $\Delta V_L$ is the value of $V_L$ at the point where $Q(t)$ crosses zero for the last time during the extension time interval or the start of the ventilator's exhalation phase. The beginning point for $\Delta V_L$ is the value of $V_L$ at the point where $Q(t)$ crosses from negative to positive for the last time in the physiological exhalation phase. $P_{eoi}$ is the value of $P_y(t)$ at the point where $Q(t)$ crosses from positive to negative for the last time in the physiological inhalation phase (typically during the extension time interval $T_{IE}$ or the start of the ventilator's exhalation phase). $P_{boi}$ is the value of $P_y(t)$ at the point where $Q(t)$ crosses from negative to positive for the last time in the physiological exhalation phase.

Figure 2:
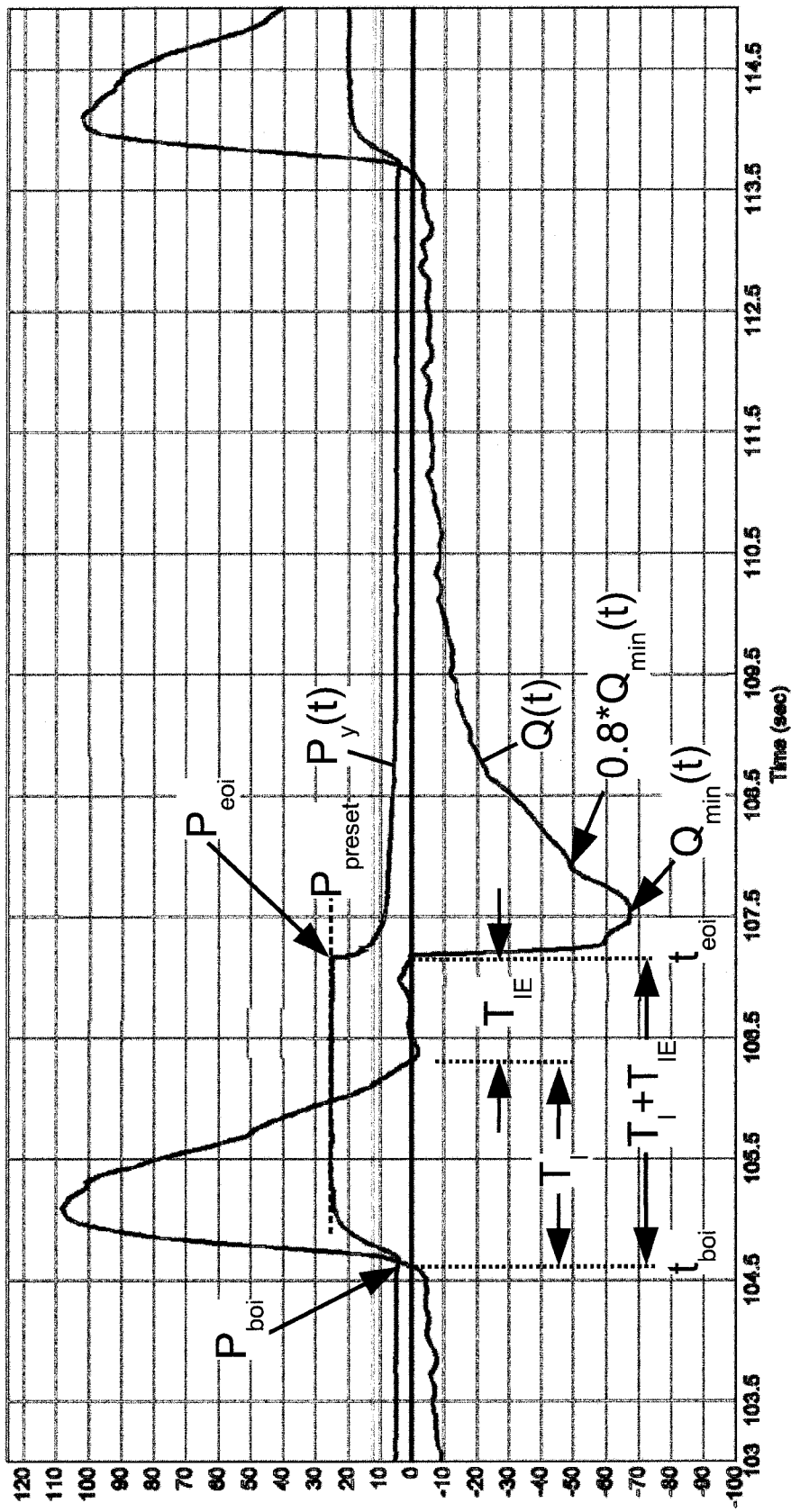
FIG. 2 plots a simulation of airway pressure $P_y(t)$ and airway flow $Q(t)$ for a passive patient (one making no respiratory effort) during performance of the respiratory system measurement process using the mechanical ventilation device of FIG. 1.

With reference to FIG. 2, the estimation of $C_L$ (or $E_L$) is described in the case of a passive patient for whom $P_{mus}(t)=0$ everywhere (the passive patient is exerting no respiratory effort). FIG. 2 plots a simulation of the airway pressure $P_y(t)$ and the airway flow $Q(t)$. As seen in FIG. 2, the pressure $P_{boi}$ is measured at the beginning of the inhalation phase, with the airway flow $Q(t)$ close to or equal to zero. Hence, the lungs are in equilibrium with the air in the hosing 20, 22 and the measured $P_{boi}$ is equal to the pressure in the lungs. With $P_{mus}(t)=0$ throughout the airway pressure $P_y(t)$ rapidly ramps up to the applied preset pressure $P_{preset}$ and is held steady at this pressure by the mechanical ventilator 10, with the exhaust valve 40 being controlled to avoid any pressure overshoot. The inhalation period $T_I$ terminates at about when the air flow $Q(t)$ returns to zero as the lungs are fully inflated (to the extent they can be inflated at pressure $P_{present}$). However, as seen in FIG. 2 the pressure-controlled breath is maintained at the pressure $P_{preset}$ for an additional extension time interval $T_{IE}$. As $P_{mus}(t)$ is zero throughout, the flow remains essentially at zero over this additional time interval $T_{IE}$. As a consequence, the measured pressure $P_{eoi}$ measured during the extension time interval $T_{IE}$ is measured with $Q(t)=0$ so that the lungs are in equilibrium with the air in the hosing 20, 22—accordingly, the measured $P_{eoi}$ is equal to the pressure in the lungs. Thus, when Equation (1) or Equation (2) is applied, the lung compliance $C_L$ or elastance $E_L$ is determined with the ending lung pressure being accurately measured by $P_{eoi}$ for the preset pressure $P_{preset}$ of the pressure-controlled therapeutic ventilation. The error introduced by the pressure overshoot is thus minimized, as is the error induced by lack of equilibrium of the pressure in the lung and that of the airway pressure at the patient's airway port or pressure measurement site.

Figure 3:
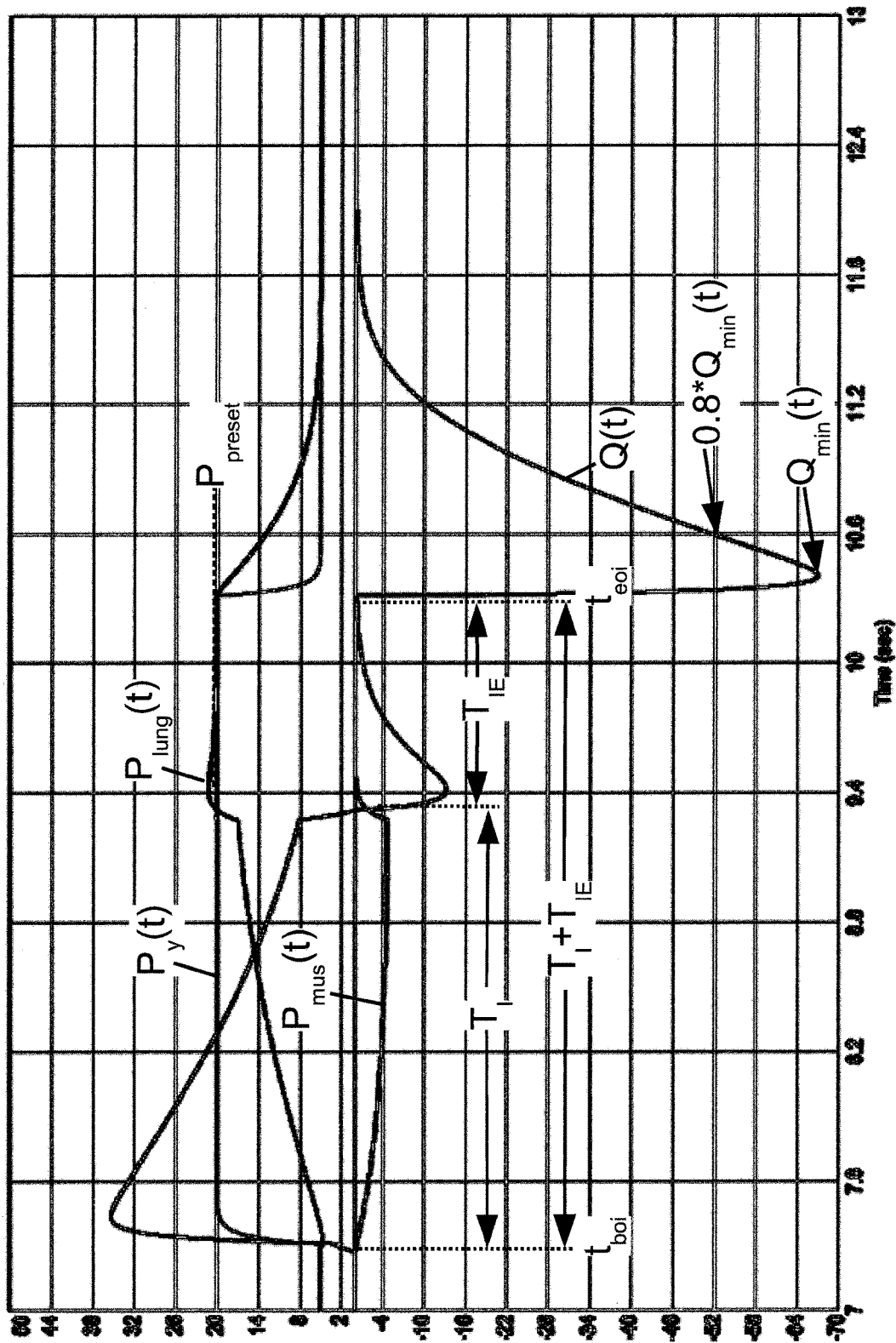
FIG. 3 plots a simulation of airway pressure $P_y(t)$ and airway flow $Q(t)$ for an active patient who is making respiratory effort producing the indicated respiratory muscle pressure $P_{mus}(t)$ during performance of the respiratory system measurement process using the mechanical ventilation device of FIG. 1.

With reference to FIG. 3, the estimation of $C_L$ (or $E_L$) is described in the case of an active patient who is actively exerting respiratory effort and hence for whom $P_{mus}(t)$ is not zero. Compared with FIG. 2, this is reflected by the additional curve $P_{mus}(t)$ plotted in the simulation of FIG. 3 along with the simulated airway pressure $P_y(t)$ and airway flow $Q(t)$. As seen in FIG. 3, the pressure $P_{boi}$ is measured at the beginning of the inhalation phase, with the airway flow $Q(t)$ close to or equal to zero. Hence, the lungs are in equilibrium with the air in the hosing 20, 22 and the measured $P_{boi}$ is equal to the pressure in the lungs. The airway pressure $P_y(t)$ then rapidly ramps up to the applied preset pressure $P_{preset}$. However, unlike the case of the passive patient of FIG. 2, in the case of the active patient of FIG. 3 the patient is applying respiratory muscle pressure $P_{mus}(t)$ which perturbs the pressure $P_y(t)$ as compared with what this pressure would otherwise be. This perturbation is compensated to hold $P_y(t) \approx P_{preset}$ by action of the exhaust valve 40 being opened as needed to (mostly) avoid any pressure overshoot. In the simulation of FIG. 3, some slight overshoot is observed in spite of this compensation; however, the overshoot is present only at around the transition from the inhalation time period $T_I$ to the extension time interval $T_{IE}$, and the pressure soon returns to $P_y(t)=P_{preset}$ by action of the controlled exhalation valve 40 suppressing the pressure overshoot. As seen in FIG. 3, the pressure-controlled breath is maintained at the pressure $P_{preset}$ for the additional extension time interval $T_{IE}$, which in the illustrative example of FIG. 3 is the time interval from the first zero crossing of the air flow $Q(t)$ to the second zero crossing of the air flow $Q(t)$. As previously noted, this comports with an approach in which $T_{IE}$ is a patient-specific value determined by measuring the time interval between successive zero crossings for several representative (calibration) breaths. This approach is again premised on the recognition that the end of physiological inspiration is associated with a reversal of air flow $Q(t)$ due to respiratory muscle recoil-generated pressure, and that by the time of the next zero crossing of the (now reversed) air flow $Q(t)$ it is known that all respiratory muscle recoil-generated pressure has vanished. As seen in FIG. 3, the airway flow at the end of physiological inspiration initially reverses, i.e. decreases to a negative number—this is accommodated by the exhaust valve 40 being opened a controlled amount to (mostly) suppress the pressure overshoot above $P_{preset}$. Near the end of the extension time interval $T_{IE}$ the respiratory muscles recoil has dissipated and $P_{mus}(t)$ has returned to zero, while the control provided by the exhaust valve 40 has maintained $P_y(t) \cong P_{preset}$. As a consequence, the measured pressure $P_{eoi}$ measured near the end of the extension time interval $T_{IE}$ is measured with $Q(t)=0$ so that the lungs are in equilibrium with the air in the hosing 20, 22—accordingly, the measured $P_{eoi}$ is equal to the pressure in the lungs. Thus, when Equation (1) or Equation (2) is applied, the lung compliance $C_L$ or elastance $E_L$ is determined with the ending lung pressure being accurately measured by $P_{eoi}$ for the preset pressure $P_{preset}$ of the pressure-controlled therapeutic ventilation. The error introduced by the pressure overshoot is thus minimized, as is the error induced by lack of equilibrium of the pressure in the lung and that of the airway pressure at the patient's airway port or pressure measurement site.

The disclosed approach for accurately measuring $C_L$ or $E_L$ for pressure-controlled ventilation mode (e.g. PSV or PCV) conditions, and in the presence of respiratory effort by the patient, leverages the expectation that the patient's respiratory effort will be expended during the inhalation phase and will rapidly dissipate (e.g. within about 0.3-0.7 sec) after end of inhalation, so that the extension time interval $T_{IE}$ of order this duration provides for accurate measurement of $P_{eoi}$ without perturbation due to patient respiratory effort. Furthermore, by applying the pressure-controlled breath at preset pressure $P_{preset}$ (which is preferably the same as the preset pressure used in the therapeutic pressure-controlled ventilation) and additionally controlling the exhalation valve 40 to suppress any pressure overshoot, it can be achieved that measurements are performed with $P_{eoi} \cong P_{preset}$ (thus mimicking actual PSV or PCV therapeutic respiratory conditions) and with $Q(t)=0$ (thus ensuring the airway pressure is an accurate surrogate for the actual lung pressure).

In short, a synergistic combination is disclosed, including: (1) applying the pressure-controlled breath at preset pressure $P_{preset}$, and (2) opening the exhalation valve 40 as needed to suppress pressure overshoot, and (3) adding the extension time interval $T_{IE}$ to the pressure-controlled breath to permit dissipation of any patient respiratory exertion which is recognized to terminate at the end of inhalation. This synergistic combination allows for accurate measurement of $C_L$ (or $E_L$) at PSV or PCV conditions in the presence of respiratory effort by the patient.

In addition to lung compliance or elastance, it is often advantageous to measure lung resistance $R_L$. Some suitable approaches for doing this are next described.

In an illustrative approach, the airway flow $Q(t)$ continuing after the end of the extension time interval $T_{IE}$ enters into the exhalation phase, where the air flow reverses (air flow exiting the lungs is negative in FIGS. 2 and 3), and is allowed to reach its minimum, designated here as $Q_{min}$. This initial phase of exhalation is not well-suited for accurate measurement of $R_L$. Instead, data for computing $R_L$ is taken starting at some point after the time of $Q_{min}$, e.g. when the exhalation air flow reaches $0.8*Q_{min}$ or thereabout in the illustrative examples. In one illustrative example, the data collection runs from the time the air flow reaches $0.8*Q_{min}$ until the air flow decreases to the larger of $0.1*Q_{min}$ and 2 liters-per-min. It is to be appreciated that this interval is merely illustrative, and other intervals can be chosen so long as the air flow is not changing at a fast pace, and thus inertial effects are avoided. For a given point in time for which $P_y(t) \rightarrow P_y$, and $Q(t) \rightarrow Q$, the resistance $R_L$ can be estimated as:

$$R_L = \frac{P_y - P_{boi}}{Q} - \frac{V_L}{C_L \cdot Q} \quad (3)$$

If $R_L$ is assumed to be independent of the airway air flow $Q$ then Equation (3) can be used directly to compute $R_L$, possibly averaging over several $(P_y(t), Q(t))$ measurements. However, in practice $R_L$ tends to vary depending upon the airway flow $Q$. To address this, in a preferred embodiment the set of estimations for $R_L$ resulting from the continuous estimation of $R_L$ in the lung flow range specified above (e.g. from flow $0.8Q_{min}$ to $0.1Q_{min}$ or until flow drops to 2 lpm), is used to find coefficients $k_0$ and $k_1$ (via regression of $R_L$ vs $Q_L$ using Least Square Estimation) for the following resistance model:

$$R_L = k_0 Q + k_1 \quad (4)$$

This assumes the lung resistance $R_L$ follows a linear dependence on airway flow $Q$. It will be appreciated that other models for the $R_L$-$Q$ dependence may be employed.

With returning reference to FIG. 1, the output of the respiratory system measurement process 44 is the lung compliance $C_L$ (or, equivalently, elastance $E_L = 1/C_L$) and the lung resistance $R_L = k_0 Q(t) + k_1$. These values may be used for various purposes. In one example, the values are input to the patient monitor 16, where they are displayed, e.g. as a trend line. In the case of $R_L$ the plot may show, for example, the value at a chosen flow Q. These trend lines can be used for various diagnostic purposes; for example, a decrease in the lung compliance $C_L$ over time can be an indicator of onset of Acute Respiratory Distress Syndrome (ARDS), while an increase in $R_L$ over time may indicate an airway narrowing.

In another embodiment, the values may be fed back to the ventilator 10. (In embodiments in which the electronic processor 14 is the ventilator microprocessor or microcontroller, no "feedback" is required). In one approach, the Equation of Motion of the Lungs is applied to estimate the respiratory muscle pressure $P_{mus}(t)$ from the measured airway pressure $P_y(t)$ and measured airway flow Q(t) and the time-integrated lung volume $V_L(t)$, along with $C_L$ and $R_L$ output by the respiratory system measurement process 44. For example, one formulation of this Equation of Motion may be written as:

$$P_{mus}(t) = Q(t) \cdot R_L + \frac{V_L(t) + V_0}{C_L} - P_y(t) \quad (5)$$

If the linear model for $R_L$-Q of Equation (4) is used then this can be written as:

$$P_{mus}(t) = Q(t) \cdot (k_0 Q(t) + k_1) + \frac{V_L(t) + V_0}{C_L} - P_y(t) \quad (6)$$

In Equations (5) and (6), $V_0$ is the volume required to elevate the pressure in the lung from ambient pressure to the Positive end-expiratory pressure (PEEP) level. The respiratory muscle pressure $P_{mus}(t)$ computed using Equation (5) or Equation (6) may be used in various ways. The Work of Breathing (WoB) can be computed as:

$$WoB = \frac{1}{T} \int_T P_{mus}(t) dV_L(t) \quad (7)$$

where the integral period T is over one breath interval. Alternatively, the Power of Breathing (PoB) can be computed over a unit time interval, such as one minute.

In the foregoing, every time a change in PEEP is carried out, $V_0$ should preferably be calculated. At the onset of ventilation, the volume required to elevate the lung pressure to the PEEP setting selected is stored for use in the respiratory system estimation. At the boi of all breaths where maneuvers are performed, the value of $V_0$ is preferably updated, e.g. according to $V_0(k)=V_0(k-1)+V_{L,eoe}(k-1)-V_{L,boi}(k-1)$ where k is the maneuver breath number and $V_{Leoe}(k-1)$ is the volume at the end of exhalation for the previous maneuver breath. The calculation of $V_L$ may be reset to zero at each maneuver breath's boi, and after $V_0(k)$ has been adjusted.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory device comprising:
an airway pressure sensor;
an airway flow sensor; and
an electronic processor programmed to control a mechanical ventilator to provide respiratory support using a pressure controlled ventilation mode and to perform a respiratory system measurement process including:
controlling the mechanical ventilator to provide a pressure controlled breath at a preset pressure over an extended inspiratory breath interval that is extended by an extension time interval beyond an end of inspiration indicated by a zero crossing of the airway flow;
controlling an exhalation valve at least during the extension time interval to maintain airway pressure estimated by the airway pressure sensor at the preset pressure;
during the extended inspiratory breath interval, acquiring airway pressure estimates from the airway pressure sensor and airway flow estimates from the airway flow sensor; and
determining lung compliance or elastance from the airway pressure estimates and the airway flow estimates acquired during the extended inspiratory breath interval;
wherein the extension time interval comprises a patient-specific extension time interval determined from the airway flow estimates acquired after end of inspiration over several breaths.

2. The respiratory device of claim 1 wherein determining lung compliance or elastance comprises:
determining an end of inhalation (eoi) airway pressure as an airway pressure estimate acquired at an eoi measurement time when the airway flow estimate is zero for the last time in the extended inspiratory period;
determining a beginning of inhalation (boi) airway pressure as an airway pressure estimate acquired at a boi measurement time at the beginning of the extended inspiratory breath interval; and
determining the lung compliance or elastance based on a ratio of:
a change in lung volume produced by the pressure controlled breath and computed as a time integral of the airway flow estimates, and
a difference between the eoi airway pressure and the boi airway pressure.

3. The respiratory device of claim 2 wherein the change in lung volume produced by the pressure controlled breath is computed as a time integral of the airway flow estimates between the boi measurement time and the eoi measurement time.

4. The respiratory device of claim 2 wherein determining lung compliance or elastance comprises determining lung compliance CL according to:

$$C_L = \frac{\Delta V_L}{P_{eoi} - P_{boi}}$$

or determining lung elastance $E_L$ according to:

$$E_L = \frac{P_{eoi} - P_{boi}}{\Delta V_L}.$$

5. The respiratory device of claim 1 wherein the respiratory system measurement process further includes:
    after the extended inspiratory breath interval, acquiring airway pressure estimates from the airway pressure sensor and airway flow estimates from the airway flow sensor; and
    determining lung resistance using the determined lung compliance or elastance and the airway pressure estimates and the airway flow estimates acquired after the extended inspiratory breath interval.

6. The respiratory device of claim 1 wherein controlling an exhalation valve comprises:
    controlling the exhalation valve over the extended inspiratory breath interval to prevent the airway pressure estimated by the airway pressure sensor from rising above the preset pressure.

7. The respiratory device of claim 1 wherein the respiratory system measurement process further includes:
    determining an inspiratory breath interval as a detected inhalation time period of a breath averaged over a defined number of breaths; and
    setting the extended inspiratory breath interval as the determined inspiratory breath interval plus the extension time interval.

8. The respiratory device of claim 1 wherein the electronic processor is programmed to control the mechanical ventilator to provide respiratory support using a pressure controlled ventilation mode selected from the group comprising pressure support ventilation (PSV) and pressure control ventilation (PCV).

9. The respiratory device of claim 1 further comprising:
    a display, wherein the electronic processor is further programmed to present on the display at least one of:
    the determined lung compliance or elastance, and
    a value computed from the determined lung compliance or elastance.

10. A ventilator device comprising:
    a mechanical ventilator;
    an airway pressure sensor;
    an airway flow sensor; and
    an electronic processor programmed to control the mechanical ventilator to provide respiratory support including applying a preset pressure during inhalation, and to perform a respiratory system measurement process including:
    controlling the mechanical ventilator to provide a pressure controlled breath at the preset pressure over an extended inspiratory breath interval that is extended by an extension time interval beyond end of physiological inspiration;
    controlling an exhalation valve during the extended inspiratory breath interval to maintain airway pressure estimated by the airway pressure sensor at the preset pressure;
    using the airway pressure sensor, measuring an end of inhalation (eoi) airway pressure at a time when the airway flow estimate is zero;
    using the airway pressure sensor, measuring a beginning of inhalation (boi) airway pressure at the beginning of the extended inspiratory breath interval; and
    determining lung compliance or elastance based on (i) a change in lung volume produced by the pressure controlled breath and computed as a time integral of airway flow estimates by the airway flow sensor and (ii) a difference between the eoi airway pressure and the boi airway pressure;
    wherein the extension time interval comprises a patient-specific extension time interval determined from the airway flow estimates acquired after end of inspiration over several breaths.

11. The ventilator device of claim 10 wherein the change in lung volume produced by the pressure controlled breath is computed as a time integral of the airway flow estimates between the boi measurement time and the eoi measurement time.

12. The ventilator device of claim 10 wherein determining lung compliance or elastance comprises determining lung compliance CL according to:
    or determining lung elastance EL according to:
    where Peoi is the eoi airway pressure, Pboi is the boi airway pressure, and is the change in lung volume produced by the pressure controlled breath.

13. The ventilator device of claim 10 wherein the respiratory system measurement process further includes:
    determining lung resistance based on the determined lung compliance or elastance and airway pressure estimates and airway flow estimates acquired after the extended inspiratory breath interval using the airway pressure sensor and the airway flow sensor, respectively.

14. The ventilator device of claim 10 wherein the extended inspiratory breath interval is extended by the extension time interval determined from airway flow estimates acquired by the airway flow sensor.

* * * * *